US006224896B1

(12) United States Patent
Redmond

(10) Patent No.: US 6,224,896 B1
(45) Date of Patent: May 1, 2001

(54) COMPOSITION AND PROCESS FOR THE TREATMENT OF EPIDERMAL TRAUMAS SUCH AS DECUBITUS ULCERS

(75) Inventor: Mary L. Redmond, Chicago, IL (US)

(73) Assignee: Curlor Healthcare Technologies, LLC, Chicago, IL (US)

( * ) Notice: Subject to any disclaimer, the term of this patent is extended or adjusted under 35 U.S.C. 154(b) by 0 days.

(21) Appl. No.: 09/122,498

(22) Filed: Jul. 24, 1998

Related U.S. Application Data
(60) Provisional application No. 60/053,908, filed on Jul. 28, 1997.

(51) Int. Cl.$^7$ .............................. A61K 9/70; A61F 13/00
(52) U.S. Cl. ......................... 424/443; 424/445; 424/446; 424/449; 424/195.1; 424/641; 424/642
(58) Field of Search .................................... 424/643, 445, 424/446, 449, 195.1, 641, 642

(56) References Cited

U.S. PATENT DOCUMENTS

| | | | |
|---|---|---|---|
| 3,996,934 | 12/1976 | Zaffaroni | 128/268 |
| 4,294,852 | 10/1981 | Wildnauer et al. | 424/317 |
| 4,341,208 | 7/1982 | Gordon | 128/156 |
| 4,584,188 | 4/1986 | Graham | 424/19 |
| 4,735,935 | 4/1988 | McAnalley | 514/53 |
| 4,803,066 | 2/1989 | Edwards | 424/132 |
| 4,837,378 | 6/1989 | Borgman | 424/81 |
| 4,909,243 | * 3/1990 | Frank et al. | 128/156 |
| 4,917,890 | 4/1990 | McAnalley | 424/195.1 |
| 4,957,907 | 9/1990 | McAnalley | 514/54 |
| 5,183,664 | 2/1993 | Ansell | 424/445 |
| 5,234,915 | 8/1993 | Mathur et al. | 517/54 |
| 5,407,670 | 4/1995 | Shinault | 424/78.06 |
| 5,409,703 | * 4/1995 | McAnalley et al. | 424/435 |
| 5,503,847 | 4/1996 | Queen et al. | 424/488 |
| 5,612,052 | 3/1997 | Shalaby | 424/426 |
| 5,618,559 | 4/1997 | Desai et al. | 424/468 |
| 5,662,924 | 9/1997 | Rhodes | 424/445 |
| 5,714,159 | 2/1998 | Shalaby | 424/426 |
| 5,714,165 | 2/1998 | Repka et al. | 424/514 |

OTHER PUBLICATIONS

PCT Preliminary Exam Report for PCT/US98/15413, mailed Sep. 2, 1999.
International Search Report for Application No. PCT/US98/15413, Dated Nov. 3, 1998.
TransiGel Conformable Hydrogel–Impregnated Dressing–Smith & Nephew–Wound Care Products–1998 (2 pages).
IntraSite* Gel–Hydrogel Wound Dressing–Smith & Nephew–Wound Care Products–1998 (2 pages).
Intrasite Gel® –Dressing Hydrogel, Amorphous–Smith & Nephew Medical Ltd. 1998 (2 pages).
Hydrocolloid Dressings–various manufacturers–(2 pages).
Hydrogel Dressings–various manufacturers–1998 (2 pages).
Review of wound management materials–Bridgend General Hospital–1996 Surgical Materials Testing Laboratory (20 pages).
Guidance on Dressing Selection–Bridgend General Hosptial–1996 Surgical Materials Testing Laboratory (20 pages).
Geriatrics–Pressure Ulcers: Prevention and Management–1996–1998 Mayo Foundation for Medical Education and Research (12 pages).
A structured approach to the selection fo dressings–Wound Management Practice–1997 (14 pages).
Carrasyn® Hydrogel Wound Dressing–Carrington Labs Wound Care Product Line–1998 (2 pages).
Wound Care Information Network, product list, 1997 (9 pages).
Rosacea Products, Galderma Canada, 1998 (11 pages).
Metronidazole use in malodorous skin lesions–Rice TT–1992 MEDLINE–Abstract.
Topical metronidazole gel: The bacteriology of decubitus ulcers Witkowski–1991 EMBASE–Abstract,
Moisture–retentive dressings: A review of the current literature–Duncan Nickerson BSC–1998 (7 pages).
Pressure sores–Vohra, R.K. ; McCollum, C.N.–Med & Health News 1994.
PCT Written Opinion for PCT/US98/15413, mailed May 27, 1999.

* cited by examiner

Primary Examiner—Thurman K. Page
Assistant Examiner—Lakshmi Channavajjala
(74) Attorney, Agent, or Firm—Sidley & Austin; Hugh A. Abrams

(57) ABSTRACT

A novel composition for use in the treatment of epidermal traumas is disclosed. The composition comprises a nitroimadazole, an occlusive skin barrier composition, and an occlusive synthetic dressing. Furthermore, the invention comprises a method of treatment of the epidermal trauma using the novel composition.

10 Claims, No Drawings

COMPOSITION AND PROCESS FOR THE TREATMENT OF EPIDERMAL TRAUMAS SUCH AS DECUBITUS ULCERS

This application claims benefit of Provisional application No. 60/053,908, filed Jul. 28, 1997.

FIELD OF INVENTION

This invention relates to a novel composition useful for the treatment of epidermal traumas. Furthermore, the invention also relates to the novel method of treatment of these epidermal traumas using the composition of the instant invention.

BACKGROUND OF THE INVENTION

Epidermal traumas include, for example, but not limited to, maladies such as pressure sores, burns, cuts, abrasions, wounds, rashes, lesions, skin conditions, skin infections and decubitus ulcers. Generally, these epidermal traumas are treated with ointments or preparations, sometimes with little or no success.

Pressure sores and decubitus ulcers are particularly painful for the patients and difficult to treat. Pressure on a area of skin for an extended time period may cause pressure sores. Generally, pressure sores occur at weight bearing sites. Patients eventually develop necrosis at these pressure sores since the pressure at the weight bearing sites can exceed local perfusion pressure. As the skin sloughs, bacteria tends to colonize at these sites. Abetted by further pressure induced necrosis, the infection tends to get deeper and deeper, possibly resulting in decubitus ulcers. Other factors which contribute to pressure sores include skin over bony prominence, anemia, malnutrition and immobilization. Pressure sores are especially prevalent among individuals incapable of moving, such as patients who are bedridden due to various infirmities such as strokes, quadriplegia, paraplegia or those who are in a coma. These patients suffer greatly from the pain caused by these wounds.

Generally, patients with pressure sores or decubitus ulcers are treated with topical antiseptics or relief of pressure by frequent turning. Sometimes topical debriding enzymes such as sutilains available under the trademark "Travase", manufactured by the Boots Company, collagenase available under the trademark "Santyl", manufactured by Knoll Pharmaceuticals, and fibrinolysin with desoxyribonuclease available under the trademark "Elase", manufactured by Fujisawa[Parke Davis] are used in the treatment of pressure sores and decubital ulcers. Various drug therapies may be prescribed dependent upon the type of infections that occur. Additionally, specialized beds that distribute the pressure more evenly may be used. As a final measure, surgical treatment may be necessary to remove the pressure sore itself.

U.S. Pat. No. 5,407,670 to Shinault discloses a topical ointment for the treatment of epidermal trauma. The topical ointment includes a mixture of polymyxin, bacitracin, neomycin, iodine and sugar. This ointment is applied daily until healing of the wound occurs. Numerous other ointments also exist for these traumas.

U.S. Pat. No. 5,503,847 discloses a hydrocolloid wound gel composition useful for cleansing and debriding wounds. The composition includes sodium carboxymethyl cellulose, pectin, propylene glycol and water. In addition, if desired, the hydrocolloid wound gel composition can contain a small amount of an antibiotic such as metronidazole, or a skin protective agent such as zinc oxide. This hydrocolloid gel is applied directly to the wound itself. Usually, the wound cavity is partially filled with the gel and sealed with an occlusive dressing.

Similarly, U.S. Pat. No. 5,662,924 discloses a wound dressing. The wound dressing contains a water insoluble, water swellable cross-linked cellulose derivative, water and a polyol component, wherein the dressing comprises a gel and the cellulose derivative which comprises less than 10% by weight of gel. The wound dressing may also include the antimicrobial agent metronidazole. The dressing is placed into the wound itself; the patent states a minimum depth of 5 mm should be achieved. The gel is then covered with additional absorbent material.

Nonetheless, despite these dressings, there exists a need for effective treatment and relief of epidermal traumas. In particular, there exists a great need for treatment and relief of pressure sores and decubitus ulcers, which is easy to use yet still effective on the wound.

SUMMARY OF THE INVENTION

The present invention is directed to a composition which can be used in the treatment of epidermal traumas. The composition comprises a nitroimadazole, an occlusive skin barrier composition and a occlusive synthetic dressing. Furthermore, the invention also comprises the method of treatment using this novel composition.

DETAILED DESCRIPTION OF THE PREFERRED EMBODIMENTS

The present invention provides for a novel composition that comprises a nitroimadazole compound, a occlusive skin barrier composition and an occlusive synthetic dressing. In addition, the present invention provides for the novel method of application of this composition for the treatment of epidermal traumas, such as decubitus ulcers.

The nitroimadazole compound used in the instant invention is metronidazole. Metronidazole has the following chemical structure:

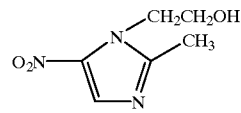

These compounds are available from numerous manufacturers including Searle under the trademark "Flagyl", Ortho under the trademark "Protostat", Fielding under the trademark "Metric 21", Lemmon under the trademark "Methyl" and McGaw under the trademark "Metro I.V." Additionally, metronidazole is also available from Zenith. It is believed that metronidazole hydrochloride as well as other analogues of metronidazole and other synthetic nitroimadazole compounds could be used in the instant invention in place of the metronidazole. The physical form of the nitroimadazole can be either powder or liquid. Further, the nitroimadazole can be placed in other carriers (i.e., for example, but not limited to other polymers, gels, liquids) provided that the efficiency of the nitroimadazole is not altered. The decision of which exact physical form of the nitroimadazole to use is well within the skill of one of ordinary skill in the art. For example, the nitroimadazole in tablet form can be dissolved in water or any other liquid that does not destroy the efficacy of the nitroimadazole for ease of application or incorporation with the other ingredients. Alternatively, the nitroimadazole if obtained in tablet form can be crushed into a powder, for effective delivery. This powder can be used alone or combined with other material(s) to form a paste.

The composition of the instant invention also includes an occlusive skin barrier composition. Any occlusive skin barrier composition can be used provided that the composition has occlusive properties. Preferably, the occlusive skin barrier composition also has antimicrobial properties. Preferably, the occlusive skin barrier composition comprises zinc oxide. Most preferably, the occlusive skin barrier comprises zinc oxide and benzethonium chloride. An example of a commercially available occlusive skin barrier comprising zinc oxide and benzethonium chloride is Critic-Aid® Antimicrobial Skin Paste, NDC 11701-030-32, manufactured by Sween.

The composition of the instant invention also includes a occlusive synthetic dressing. A variety of occlusive synthetic dressings are commercially available and used for promoting topical drug absorption and for wound healing. Generally, these dressings prevent the loss of the topical drug from the skin, promote skin hydration and increase the skin temperature. It is believed that these actions enhance penetration of certain medications. Examples of occlusive synthetic dressings include polyurethane transparent occlusive semipermeable dressings, hydrogels, dimethylpolysiloxanes and hydrocolloids. Preferably, hydrogel occlusive synthetic dressings are used. An example of a commercially available hydrogel is Carrasyn® Hydrogel Wound Dressing (NDC 053303-010-30) manufactured by Carrington Laboratories. It is believed that the Carrasyn® Hydrogel Wound Dressing is manufactured from aloe extracts as set forth in U.S. Pat. Nos. 4,917,890, 4,735,935, and 4,957,907. Therefore, alternatively, in place of the occlusive synthetic dressing, it is believed any ointment or lotion mixture containing aloe vera can be use. Examples of other aloe vera lotions or ointments that are commercially available include, but are not limited to, Aloe Vista Protective Ointment.

The ingredients of the composition can be applied individually to the epidermal trauma in a stepwise manner or prepared prior to application into various application forms for ease of use. Examples of possible application forms include ointments, salves, creams, gels, sticks, sprays, or powders.

Further, the ingredients of the composition can be placed on a patch, including, for example but not limited to, a time release patch. If ingredients are placed upon the patch, the ingredients may be layered with each particle of ingredient separated from the others with a gauze pad or like material. Moreover, the composition of the instant invention can be placed on gauze pads such as band aid pads and telfa pads. Alternatively, the ingredients of the composition may be placed in a kit having the component parts capable of being used in the treatment of the epidermal traumas. The final application form of the composition is well within the purview of one of ordinary skill in the art.

Additional ingredients may be added to the composition, provided that they do not adversely effect the efficacy of the composition or the desired result obtained by the composition on patients with epidermal traumas. Additional ingredients may include, but are not limited to, fillers, antibiotics, antimicrobials, fungicides, dyes, absorbing beads and granules.

In addition to the novel composition, the instant invention also comprises the method of treating epidermal traumas using the novel composition.

The method of treatment using the composition is quite simple. Prior to the application of the composition and the use of the method, the area of the epidermal trauma of the patient should be thoroughly cleaned. The area can be cleaned with soap and water or any other antimicrobial cleaning wipes. Care should be taken to make sure that soap is not placed in the wound itself if the wound is open. Alternatively, the wound can be cleaned with pre-moistened disposable cleaning wipes. After the wound is cleaned, the method of treatment is started.

Various steps can be used. These include placing the composition on or around the wound, and wrapping the composition with gauze pads or bandages. Alternatively, the metronidazole can be sprinkled into the wound itself, if in powder form, or sprayed, if in liquid form, or placed onto the gauze pads which will be packed into the wound. An occlusive skin barrier is gently placed or spread around the wound area and then the entire wound area is covered with gauze containing the occlusive synthetic dressing. Alternatively, the occlusive skin barrier and occlusive synthetic dressing can be mixed together before application around the wound area and coverage of the wound area with gauze.

Alternatively, all the ingredients of the composition can be applied to the dressing or gauze pad itself or a patch and then applied to the patient. In the case of deep decubitus ulcers, if a patch or dressing is used, it may be beneficial to lightly pack the ulcer with other gauze pads that have been rolled after being soaked in or sprayed with a solution made from the metronidazole. The amount of the composition and the frequency of application depend upon the individual circumstances and the severity of the epidermal condition being treated. The composition may be applied once a day. It is believed that the wound with the composition should be disturbed as little as possible. Improvement may be noticed in a few days depending upon the severity of the trauma.

The following non-limiting examples serve to illustrate the invention in further detail.

EXAMPLES

Example 1

The composition of the instant invention and the method of the application of the composition was used in the treatment of decubitus ulcers of a bed ridden patient in this example.

One 500 milligram tablet of Metronidazole, manufactured by Zenith, was dissolved in 1000 milliliter bottle of 0.9% Sodium Chloride Irrigation U.S.P. Water (#2F7123, NDC 0338-0048-03), available from the Baxter Corporation. The tablet was dissolved completely in the bottle to form a Metronidazole solution.

The area around the ulcers of the patient was washed with tap water and Ivory® soap using a face towel. Only the outside of the ulcer was washed.

Dry gauze pads were unfolded by the person administering the treatment and were stuffed loosely into a disposable container. The gauze pads were 8 ply non-sterile pads, 4 inches by 4 inches (10 cm.×10 cm.) made by Kendall Curex (#7704). The Metronidazole solution was poured over the dry gauze pads in order to soak the pads in the disposable container. The gauze pads were in solution for a few minutes until they were soaked with the Metronidazole solution.

One gauze pad was removed at a time and squeezed lightly to remove excess solution and unfolded. The pads were stacked one on top of the other. The height of the stack was dependent upon the depth of the decubitus ulcer. Each stack of pads was then rolled together lengthwise.

A separate stack of pads was then lightly placed into each decubitus ulcer. Care was taken not to pack the ulcer too tightly and to leave some of the stack to extend outside the ulcer itself. Approximately one inch of the stack was visible and extended from the decubitus ulcer when in place.

Approximately one half a teaspoon of the Critic-Aid® Antimicrobial Skin Paste was then measured. The paste was spread in a circle around the wound area, but not on the ulcer itself. Additional gauze pads soaked in the metronidazole solution were unfolded and excess metronidazole solution squeezed out. These gauze pads were unfolded one at a time and placed upon the patient in order to cover the circle of the Critic-Aid® Antimicrobial Skin Paste and the decubitus ulcer packed with gauze pads.

A sufficient number of dry gauze pads to cover the decubitus ulcer were unfolded near the patient. Approximately one quarter of a teaspoon of Carrasyn® Hydrogel Wound Dressing was placed on each dry gauze pad. The dressing was spread over each dry gauze pad from edge to edge. One at a time, the gauze pads were placed over the wet gauze pads soaked in the metronidazole solution covering the decubitus ulcer and the circle of Critic-Aid® Antimicrobial Skin Paste until the entire area was covered.

These pads were kept on the patient for a minimum of twenty four hours. After twenty four hours, the treatment was re-applied. This procedure continued approximately several months, until the decubitus ulcers were eliminated. It is believed that treatment should continue after the elimination of the ulcers, possibly on a weekly basis to prevent the reappearance of the decubitus ulcers.

Example 2

Another method for possible treatment of decubitus ulcers of a bedridden patient is described in this example. The area around the decubitus ulcer of the patient is washed with warm tap water. A spray nozzle or other means to impart a mist are placed upon a bottle of 0.9% sodium chloride irrigation U.S.P. water. The entire area of the decubitus ulcer is sprayed with the 0.9% sodium chloride irrigation U.S.P. water. If desired, the ulcer itself is sprayed. It is believed that a solution of boric acid can be used in place of the sodium chloride irrigation U.S.P. water. Next, a crushed or powdered metronidazole tablet is sprinkled onto a dry gauze pad. Preferably, the 8-ply non-sterile pads, 4 inches×4 inches, made by Kendall Curex are used. The crushed metronidazole is placed only on the first gauze pad, with additional pads being stacked on top of the first gauze pad as well as one on top of other pads. The height of the stack is dependant upon the depth of the decubitus ulcer which is to be filled with the gauze. Each stack of the pads are then rolled together lengthwise for packing into the decubitus ulcer as described above in Example 1.

Approximately one half a teaspoon of Critic Aid® antimicrobial skin paste is combined with a quarter teaspoon of the Carrasyn® hydrogel wound dressing. A circle of the combination mixture is applied around the wound area. Care must be taken not to place the combination mixture in the wound area itself.

Additional gauze pads are then unfolded one at a time. Alternatively, a large roll of stretchy gauze material can be used. The gauze pad closest to the wound is sprayed with the 0.9% sodium chloride irrigation U.S.P. water. The entire area of the decubitus ulcer is covered with the gauze material.

The gauze pads or the gauze material should be kept on the patient for as long as possible. Preferably, the pads are kept on the patient for at least twenty-four hours. Furthermore, it is recommended that the patient is not turned during that time period.

Example 3

The area of the epidermal trauma such as the decubitus ulcer is washed with warm tap water and Ivory® soap. The area is rinsed with tap water and dried thoroughly using a towel or other drying means. The entire area, including the epidermal trauma are sprayed with 0.9% sodium chloride irrigation U.S.P. water until moist.

A patch containing a mixture of zinc oxide, crushed metronidazole and Carrasyn® hydrogel wound dressing is placed on the epidermal trauma.

Those skilled in the art to which the invention pertains may make modifications and other embodiments employing the principles of this invention without departing from its spirit or essential characteristics, particularly upon considering the foregoing teachings. The described embodiments are to be considered in all respects only as illustrative and not restrictive and the scope of the invention is, therefore, indicated by the appended claims rather than by the foregoing description. Consequently, while the invention has been described with reference to particular embodiments, modifications of structure, sequence, materials and the like would be apparent to those skilled in the art, yet still fall within the scope of the invention.

What is claimed is:

1. A composition for treating epidermal traumas, said composition formed in several adjacent layers applied onto a bandage or a patch comprising: a first wound-treating layer including a nitroimadazole compound; a second occlusive skin barrier layer including zinc oxide and a third occlusive synthetic dressing layer including aloe vera, said first layer being adjacent said second layer, said second layer being adjacent said third layer, and said third layer being applied onto a bandage or a patch.

2. A composition according to claim 1, wherein said nitroimadazole compound comprises metronidazole.

3. A kit for treating epidermal traumas containing: a nitroimadazole compound in a first wound contacting treatment layer; an occlusive skin barrier including zinc oxide in a second layer, an occlusive synthetic dressing including aloe vera in a third layer, said first and third layers being formed on separate pads of gauze.

4. A kit according to claim 3, wherein said nitroimadazole compound comprises metronidazole.

5. A patch for use on epidermal traumas containing a nitroimadazole compound in a first wound-contacting layer, a second occlusive skin barrier layer including zinc oxide and a third occlusive synthetic dressing layer including aloe vera.

6. A patch as claimed in claim 5, wherein said nitroimadazole compound comprises metronidazole.

7. A method of treating epidermal traumas comprising:
    cleaning a epidermal trauma;
    drying said epidermal trauma;
    soaking gauze pads in a nitroimadazole compound solution;
    forming a first treatment layer in said epidermal trauma by placing the soaked pads into contact with said epidermal trauma;
    forming a second treatment layer by circling the epidermal trauma with an occlusive skin barrier, said occlusive skin barrier including zinc oxide, said second treatment layer having said occlusive skin barrier being spaced from contact with said epidermal trauma;
    placing an occlusive synthetic dressing of aloe vera on a dry gauze pad;

forming a third treatment layer overlaying said first and second layers by placing said dry gauze pad over said epidermal trauma.

8. A method according to claim 7, wherein said nitroimadazole compound comprises metronidazole.

9. A method for treating epidermal traumas comprising:

cleaning a epidermal trauma;

spraying the epidermal trauma with water containing sodium chloride;

placing nitroimadazole on a gauze pad;

placing several additional gauze pads on top of the gauze pad containing nitroimadazole so that the stack of pads is as deep as the epidermal trauma;

rolling the stack of pads together lengthwise;

packing the epidermal trauma with the stack of pads;

mixing an occlusive skin barrier including zinc oxide and an occlusive synthetic dressing including aloe vera;

placing the mixture of said occlusive skin barrier and said occlusive synthetic dressing around said epidermal trauma ensuring that the mixture is not placed into or on said epidermal trauma;

covering said epidermal trauma.

10. A method for treating epidermal traumas comprising:

cleaning the epidermal trauma;

drying the epidermal trauma;

spraying the epidermal trauma with water containing sodium chloride;

placing a patch containing nitroimadazole in a first treatment layer, an occlusive skin barrier including zinc oxide in a second layer and an occlusive skin dressing including aloe vera in a third layer on said epidermal trauma.

* * * * *